US00PP24645P2

(12) United States Plant Patent
Blom

(10) Patent No.: US PP24,645 P2
(45) Date of Patent: Jul. 15, 2014

(54) CHRYSANTHEMUM PLANT NAMED 'ZANMUTUMGLOW'

(50) Latin Name: ***Chrysanthemum×morifolium* Ramat.**
Varietal Denomination: Zanmutumglow

(71) Applicant: Chrysanthemum Breeders Association Research B.V., Aalsmeer (NL)

(72) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 1 day.

(21) Appl. No.: 13/694,696

(22) Filed: Dec. 26, 2012

(51) Int. Cl.
*A01H 5/00* (2006.01)

(52) U.S. Cl.
USPC ..... Plt./290

(58) Field of Classification Search
USPC ..... Plt./290
See application file for complete search history.

*Primary Examiner* — Anne Grunberg
(74) *Attorney, Agent, or Firm* — Steptoe & Johnson LLP

(57) ABSTRACT

A *chrysanthemum* plant named 'Zanmutumglow' characterized by its medium sized blooms with orange ray florets and prolific branching; natural season flowering date September 12 (week 37); blooming for a period of 5 weeks.

3 Drawing Sheets

Botanical designation: *Chrysanthemum×morifolium* Ramat.

Cultivar denomination: 'Zanmutumglow'.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmutumglow'. 'Zanmutumglow' is a product of a breeding and selection program for outdoor pot mums (garden mums) which had the objective of creating new cultivars with a double type inflorescence, a natural season flowering date around September 12 (week 37), blooming for a period of 5 weeks. 'Zanmutumglow' is a seedling resulting from a cross of the female parent id 24631 with the male parent id 24601. Plants of the new cultivar 'Zanmutumglow' differ from plants of the female parent in the color of the ray-florets; the ray-florets of the seedling are more intensively orange colored than those of the female parent. Plants of the new cultivar 'Zanmutumglow' differ from plants of the male parent in the following characteristics. (1) Plant shape. And (2) Inflorescence type. (1) Plants of the seedling are more ball shaped, while those of the male parent are more erect. (2). The inflorescence type of the seedling is double, while that of the male parent is semi-double.

The new and distinct cultivar was discovered and selected as a flowering plant by Wilhelmus Bernardus Blom on a cultivated field in Rijsenhout, The Netherlands in September 2007. The first act of asexual production of 'Zanmutumglow' was accomplished when vegetative cuttings from the initial selection in 2007 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* (of about 16 weeks) is shown in the accompanying drawings, the color being as nearly true as possible with color photographs of this type.

DESCRIPTION OF THE INVENTION

Figure 1:
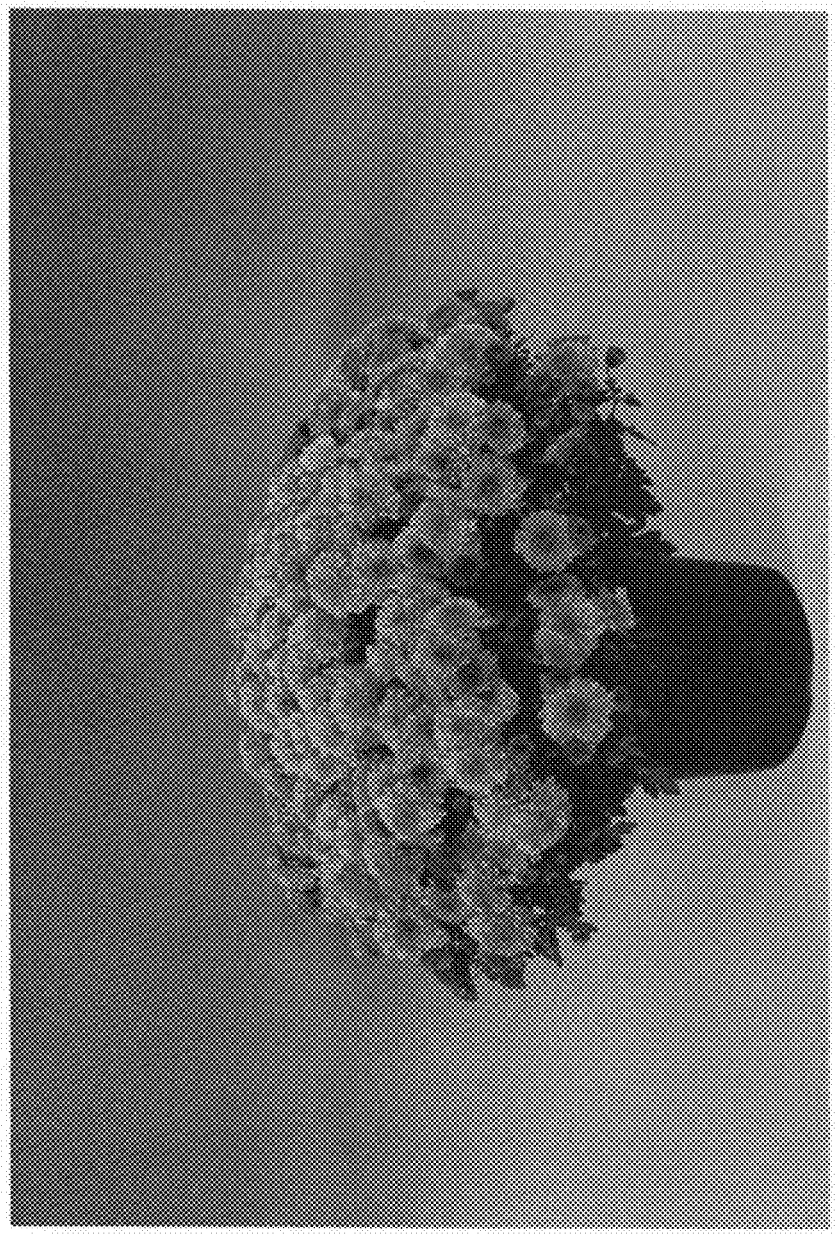
FIG. 1 shows a plant of the cultivar in full bloom.
Figure 2:
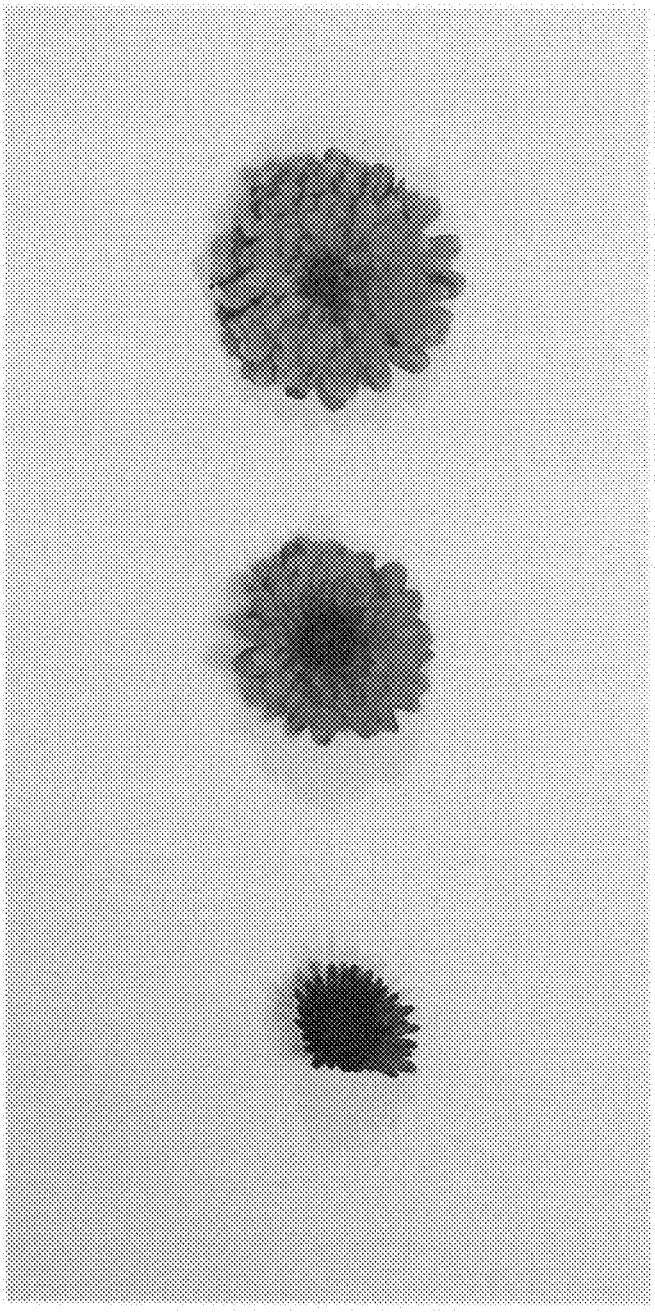
FIG. 2 shows the various stages of bloom of the new cultivar.
Figure 3:
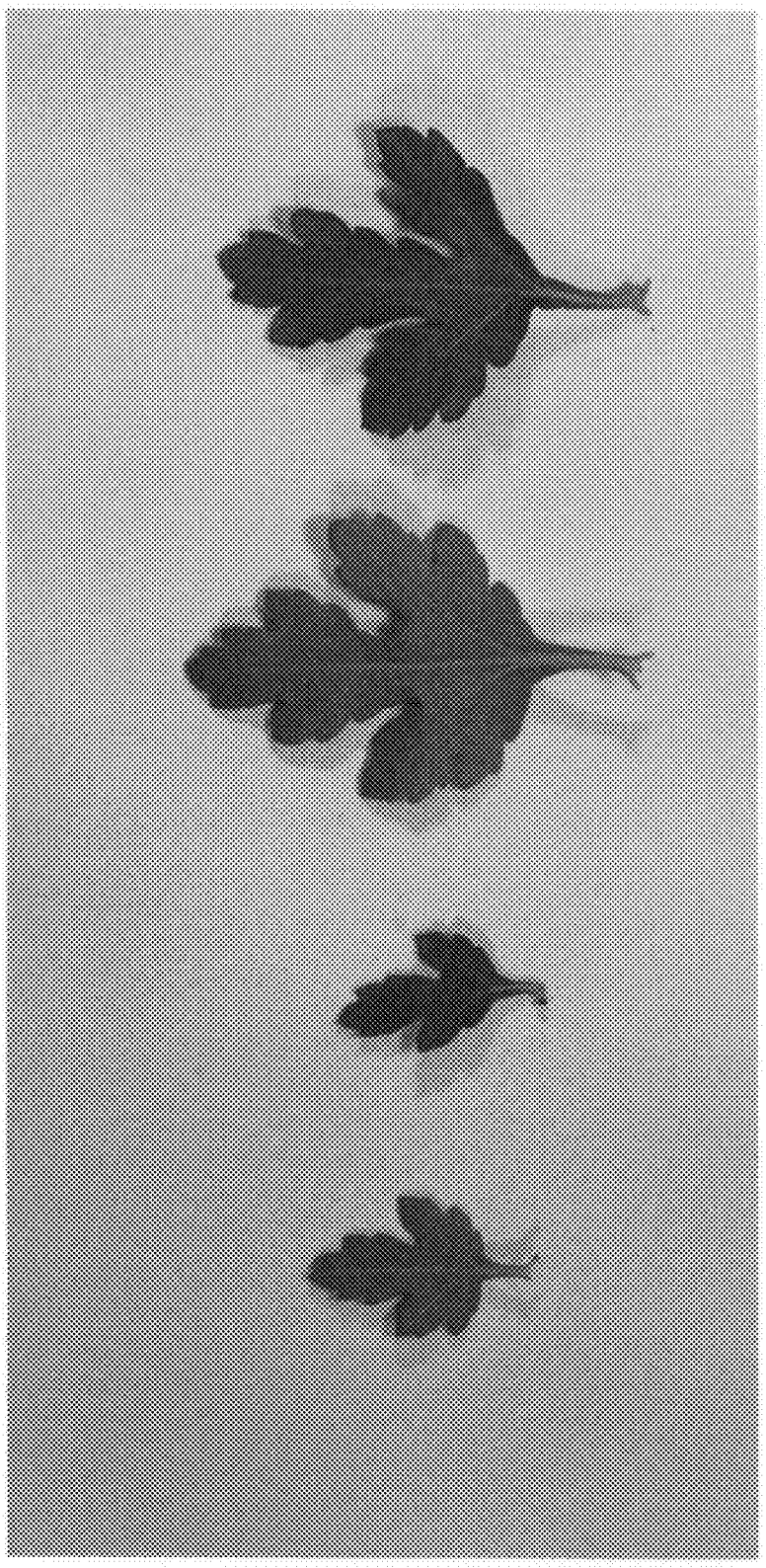
FIG. 3 shows the various stages of foliage of the new cultivar.

The observations and measurements were gathered from plants grown out door in Rijsenhout, The Netherlands under natural day length and temperature and planted in week 22 in 2011. The natural blooming date of this crop was September 12 (week 37) . The average height of the plants was 25 cm. No growth retardants were used. No tests were done on disease or insect resistance or susceptibility. No tests were done on cold or drought tolerance. This new variety produces medium sized blooms with orange ray florets blooming for a period of 5 weeks.

From the cultivars known to inventor the most similar existing cultivar in comparison to 'Zanmutumglow' is 'Zanmubedaz' (U.S. Plant Pat. No. 23,014). When 'Zanmubedaz' and 'Zanmutumglow' are being compared the following differences are noticed: The differences of 'Zanmubedaz' and 'Zanmutumglow' are (1) Number ray-florets. And (2) Vigour (1) The number of ray-florets is lower in 'Zanmubedaz' than in 'Zanmutumglow'. (2) Plants of 'Zanmubedaz' are more vigorous than those of 'Zanmutumglow'.

The following is a description of the plant and characteristics that distinguish 'Zanmutumglow' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* × *morifolium* Ramat. 'Zanmutumglow'

| | |
|---|---|
| **Bud** | |
| Size: | Small; cross-section 6 mm, height 6 mm |
| Shape: | Round |
| Texture: | Pubescent |
| Outside color: | Greyed-green 191A |
| **Phyllaries** | |
| Number: | 24, arranged in 3 rows |
| Shape: | Elliptic |
| Apex: | Acute |
| Base: | Truncate |
| Margin: | Entire |
| Color: | Upper side: Green 141C<br>Lower side: Green 141B |
| Length and width: | 5-6 mm; 2 mm |
| Texture: | Pubescent |
| **Inflorescences** | |
| Type: | Double |
| Height: | 2 cm |
| Diameter: | 4.5-5 cm |
| Peduncle length: | 3-5 cm |
| Peduncle color: | Green 138B |
| Peduncle diameter: | 1.5-2 mm |
| Peduncle texture: | Pubescent |
| Number per branch: | Approx. 7 inflorescences |
| Duration of flowering: | 5 weeks |
| Seeds: | Produced in small quantities, ovate, Greyed-brown 199A, length 1.5 mm, diameter 0.5 mm |
| Fragrance: | Faint *chrysanthemum* odor |
| **Color inflorescences** | |
| Center of inflorescence: | Immature stage: Greyed-red 181A;<br>Mature stage: Greyed-orange 172A |
| Color of upper side of ray florets: | Greyed-orange N170A |
| Color of lower side of ray florets: | Greyed-orange N170B |
| Tonality from distance: | A garden mum with orange blooms and a bronze center |
| Color of ray florets after aging of the plant: | Greyed-orange 163C |
| **Ray florets** | |
| Texture: | Upper and lower side smooth |
| Number: | 230-240 |
| Shape: | Elliptic |
| Apex: | Dentate |
| Base: | Attenuate |
| Cross-section: | Flat |
| Longitudinal axis: | Straight |
| Length of corolla tube: | 2 mm |
| Ray floret margin: | Entire |
| Ray floret length: | 1.5-2.2 cm |
| Ray floret width: | 4-5 mm |
| Ratio length/width: | Medium |
| Disc florets | Absent |
| **Receptacle** | |
| Color: | Yellow-green 145D |
| Shape: | Domed raised |
| Height: | 4 mm |
| Diameter: | 3 mm |
| **Reproductive Organs** | |
| Androecium: | Absent |
| Gynoecium: | Present in ray florets |
| Style color: | Yellow-green 154C |

TABLE 1-continued

Botanical Description of *Chrysanthemum* × *morifolium* Ramat. 'Zanmutumglow'

| | |
|---|---|
| Style length: | 3 mm |
| Stigma color: | Yellow 7A |
| Stigma width: | 1 mm |
| Ovary: | Enclosed in calyx |
| **Plant** | |
| Form: | Grown as a spray type pot mum, outdoor raised and mounded |
| Growth habit: | Spherical shape |
| Growth rate: | Low to medium |
| Height: | 25 cm |
| Width: | 35-40 cm |
| Stem color: | Greyed-brown 199A |
| Stem strength: | Medium |
| Stem brittleness: | Brittle |
| Stem anthocyanin coloration: | Not observed |
| Internode length: | 1.5-2.5 cm |
| Length of lateral branch: | From top to bottom 12-14 cm |
| Lateral branch color: | Green 137 C |
| Lateral branch, attachment: | Brittle |
| Lateral branch diameter: | 2.5 mm |
| Branching (average number of lateral branches): | Prolific with 8 breaks after pinching |
| Natural season blooming date: | September 12 (week 37-41) |
| **Foliage** | |
| Leaf color: | Upper side: Green 138A;<br>Lower side: Green 137C |
| Color midvein: | Upper side: Yellow-green 147D;<br>Lower side: Yellow-green 148D |
| Size: | Small; length 3.5-5 cm, width 2.2-3.5 cm |
| Quantity (number per lateral branches): | 10-12 |
| Shape: | Elliptic |
| Texture upper side: | Sparsely pubescent |
| Texture under side: | Pubescent |
| Venation arrangement: | Palmate |
| Shape of margin: | Serrated |
| Shape of base of sinus between lateral lobes: | Rounded |
| Margin of sinus between lateral lobes: | Diverging |
| Shape of base: | Truncate |
| Apex: | Mucronulate |
| Petiole length: | 0.6-1 cm |
| Petiole diameter: | 2-2.5 mm |
| Petiole color: | Yellow-green 147D |

TABLE 2

Differences with the comparison variety (when grown under identical conditions)

| | 'Zanmutumglow' | 'Zanmubedaz' |
|---|---|---|
| Number ray-florets | 230-240 | 210 |
| Width plants | 35-40 cm | 40-45 cm |

I claim:

1. A new and distinct *chrysanthemum* plant named 'Zanmutumglow' as described and illustrated.

* * * * *